United States Patent
Taylor et al.

(10) Patent No.: US 12,167,895 B2
(45) Date of Patent: Dec. 17, 2024

(54) SAFETY FEATURE FOR USE WITH ROBOTICALLY MANIPULATED ENDOSCOPES AND OTHER TOOLS IN OTOLARYNGOLOGY AND NEUROSURGERY

(71) Applicant: THE JOHNS HOPKINS UNIVERSITY, Baltimore, MD (US)

(72) Inventors: Russell H. Taylor, Severna Park, MD (US); Francis Xavier Creighton, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 885 days.

(21) Appl. No.: 17/265,415

(22) PCT Filed: Aug. 2, 2019

(86) PCT No.: PCT/US2019/044787
§ 371 (c)(1),
(2) Date: Feb. 2, 2021

(87) PCT Pub. No.: WO2020/028747
PCT Pub. Date: Feb. 6, 2020

(65) Prior Publication Data
US 2021/0298839 A1   Sep. 30, 2021

Related U.S. Application Data

(60) Provisional application No. 62/713,747, filed on Aug. 2, 2018.

(51) Int. Cl.
*A61B 34/30* (2016.01)
*A61B 1/00* (2006.01)
(Continued)

(52) U.S. Cl.
CPC .......... *A61B 34/20* (2016.02); *A61B 1/00149* (2013.01); *A61B 5/0002* (2013.01);
(Continued)

(58) Field of Classification Search
CPC ............ A61B 1/00006; A61B 1/00149; A61B 5/0002; A61B 5/1113; A61B 5/1126;
(Continued)

(56) References Cited

U.S. PATENT DOCUMENTS 5,086,401 A   2/1992  Glassman et al.
6,102,850 A * 8/2000  Wang ..................... A61B 34/30
                                                600/102
(Continued)

FOREIGN PATENT DOCUMENTS

CN      10458269 B     5/2017
RU      135957 U1     12/2013
(Continued)

OTHER PUBLICATIONS

Kozin et al., "Systematic review of outcomes following observational and operative endoscopic middle ear surgery", Laryngoscope, vol. 125-6, pp. 1205-1214, May 2015.
(Continued)

*Primary Examiner* — Daniel L Cerioni

(57) ABSTRACT

The present invention is directed to a system to improve the safety of robotically assisted minimally invasive surgery. The system includes an endoscope holder, an accelerometer, and a controller. The accelerometer is configured to track motion of the patient's head and transmit that information to the controller. The controller is configured to operate the endoscope holder. When the accelerometer detects patient head movement, the controller then retracts the endoscope, via the endoscope holder. The system of the present invention can be used for endoscopic surgery for otolaryngology (Continued)

and neurosurgery. It can also be used for other surgical situations with similar requirements and constraints.

20 Claims, 3 Drawing Sheets

(51) Int. Cl.
    *A61B 5/00*         (2006.01)
    *A61B 5/11*         (2006.01)
    *A61B 34/20*       (2016.01)

(52) U.S. Cl.
    CPC ........... *A61B 5/1113* (2013.01); *A61B 5/1126* (2013.01); *A61B 5/6831* (2013.01); *A61B 5/6832* (2013.01); *A61B 34/30* (2016.02); *A61B 2034/2048* (2016.02); *A61B 2034/301* (2016.02); *A61B 2562/0219* (2013.01)

(58) Field of Classification Search
    CPC ..... A61B 5/6831; A61B 5/6832; A61B 34/20; A61B 34/30; A61B 90/50; A61B 2034/2048; A61B 2034/2051; A61B 2034/2055; A61B 2034/301; A61B 2090/3983; A61B 2562/0219
    See application file for complete search history.

(56) References Cited

U.S. PATENT DOCUMENTS

| | | | |
|---|---|---|---|
| 9,554,865 | B2 | 1/2017 | Olds et al. |
| 2005/0222612 | A1 | 10/2005 | Vries et al. |
| 2008/0029577 | A1* | 2/2008 | Shelton ................ A61B 17/072 227/176.1 |
| 2009/0024142 | A1 | 1/2009 | Ruiz Morales |
| 2011/0092857 | A1 | 4/2011 | Herscovici-Cohen et al. |
| 2011/0144456 | A1 | 6/2011 | Muhlsteff et al. |
| 2014/0153794 | A1 | 6/2014 | Varaklis |
| 2016/0262687 | A1* | 9/2016 | Vaidyanathan ...... A61B 5/0205 |
| 2017/0296183 | A1* | 10/2017 | Shelton, IV ......... A61B 17/068 |
| 2018/0008359 | A1* | 1/2018 | Randle .................. A61B 34/32 |
| 2019/0201137 | A1* | 7/2019 | Shelton, IV ........... G16H 50/20 |

FOREIGN PATENT DOCUMENTS

| | | |
|---|---|---|
| WO | 2010140130 A1 | 12/2010 |
| WO | 2012018816 A2 | 2/2012 |

OTHER PUBLICATIONS

Taylor et al., "Taming the Bull: Safety in a Precise Surgical Robot", in Intl. Conf. on Advanced Robotics (ICAR), Pisa, Italy, Jun. 1991.

Taylor et al., "An Image-directed Robotic System for Precise Orthopaedic Surgery", IEEE Transactions on Robotics and Automation, vol. 10-3, pp. 261-275, 1994.

Paul et al., "A Surgical Robot for Total Hip Replacement Surgery", in Int. Conference on Robotics and Automation, Nice, France, May 1992.

Olds., Robotic Assistant Systems for Otolaryngology-Head and Neck Surgery, PhD thesis in Biomedical Engineering, Johns Hopkins University, Baltimore, Mar. 2015.

Olds et al., "Preliminary Evaluation of a New Microsurgical Robotic System for Head and Neck Surgery", in IEEE Int. Conf on Intelligent Robots and Systems (IROS), Chicago, Sep. 14-18, 2014. pp. 1276-1281.

* cited by examiner

SAFETY FEATURE FOR USE WITH ROBOTICALLY MANIPULATED ENDOSCOPES AND OTHER TOOLS IN OTOLARYNGOLOGY AND NEUROSURGERY

CROSS-REFERENCE TO RELATED APPLICATIONS

This application is a 35 U.S.C. § 371 U.S. national entry of International Application PCT/US2019/044787 having an international filing date of Aug. 2, 2019, which claims the benefit of U.S. Provisional Application No. 62/713,747, filed Aug. 2, 2018, the content of each of the aforementioned applications is herein incorporated by reference in their entirety.

FIELD OF THE INVENTION

The present invention relates generally to surgical instruments. More particularly, the present invention relates to a safety feature for use with robotically manipulated endoscopes and other tools in otolaryngology and neurosurgery.

BACKGROUND OF THE INVENTION

There has been an increase in the use of operative endoscopes in the field of otology. This technique uses rigid endoscopes instead of traditional microscopes to offer an improved field of view, which aides in surgeons' ability to identify and treat pathologies of the tympanic membrane, middle ear, mastoid and petrous apex.

One of the drawbacks to this surgical technique is that in order to control the endoscope and operate at the same time, the surgeon must dedicate one of his/her hands to hold the endoscope. This leaves only one free hand to perform dissection. One handed techniques cause inefficiency, as the surgeon must change instruments in the one free hand in order to suction away any blood or debris created during surgical dissection. One handed techniques also increase the difficulty of placing implants and grafts. While many different techniques have been developed to circumvent this shortcoming, such as surgical instruments designed specifically for endoscopic dissection, the lack of two-handed surgery is a significant deficit to the endoscopic approach.

Accordingly, there is a need in the art for a safety feature for use with robotically manipulated endoscopes and other tools in otolaryngology and neurosurgery.

SUMMARY OF THE INVENTION

The foregoing needs are met, to a great extent, by the present invention which provides a system for providing safety during surgery including an accelerometer configured to track patient motion. The system includes a surgical device holder. The surgical device holder includes a mechanism configured to move a surgical device disposed within the surgical device holder between a deployed position and a retracted position. The system also includes a controller configured to receive information from the accelerometer. The controller is further configured to actuate the surgical device holder between the deployed position and the retracted position, when the accelerometer detects patient motion.

In accordance with an aspect of the present invention, the mechanism of the surgical device holder includes a spring. The surgical device holder takes the form of an endoscope holder. The mechanism of the surgical device holder is configured to actuate movement of the surgical device along a longitudinal axis of the surgical device. The surgical device holder is configured to be coupled to a surgical robot or passive instrument holder. The accelerometer includes a means for coupling the accelerometer to the patient. The means for coupling the accelerometer to the patient includes one selected from a group of an elastic band, an adhesive, and screws. The accelerometer includes wireless communication with the controller, and the controller includes wireless communication with the mechanism of the surgical device holder.

In accordance with another aspect of the present invention, a system for providing safety during surgery includes a device for tracking patient motion. The system also includes a surgical device holder. The surgical device holder takes the form of a mechanism configured to move a surgical device disposed within the surgical device holder between a deployed position and a retracted position. A controller is configured to receive information from the device for tracking patient motion, wherein the controller is further configured to actuate the surgical device holder between the deployed position and the retracted position, when the device for tracking patient motion detects patient motion.

In accordance with yet another aspect of the present invention, the mechanism of the surgical device holder includes a spring. The surgical device holder takes the form of an endoscope holder. The mechanism of the surgical device holder is configured to actuate movement of the surgical device along a longitudinal axis of the surgical device. The surgical device holder is configured to be coupled to a surgical robot. The surgical device holder can also be coupled to a passive instrument holder. The device for tracking patient motion includes a means for coupling the device to the patient. Alternately, a computer vision or vision-based tracking system can also be used. The device for tracking patient motion takes the form of one selected from a group consisting of an accelerometer, video camera, auxiliary camera, and optical or electromagnetic tracking device. The device for tracking patient motion includes wireless communication with the controller. The controller includes wireless communication with the mechanism of the surgical device holder.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a system to improve the safety of robotically assisted minimally invasive surgery. One preferred embodiment of the system includes an endoscope holder, an accelerometer, and a controller. The accelerometer is configured to track motion of the patient's head and transmit that information to the controller. The controller is configured to operate the endoscope holder. When the accelerometer detects patient head movement, the controller then retracts the endoscope, via the endoscope holder. The system of the present invention can be used for endoscopic surgery for otolaryngology and neurosurgery. It can also be used for other surgical situations with similar requirements and constraints.

Figure 1A:
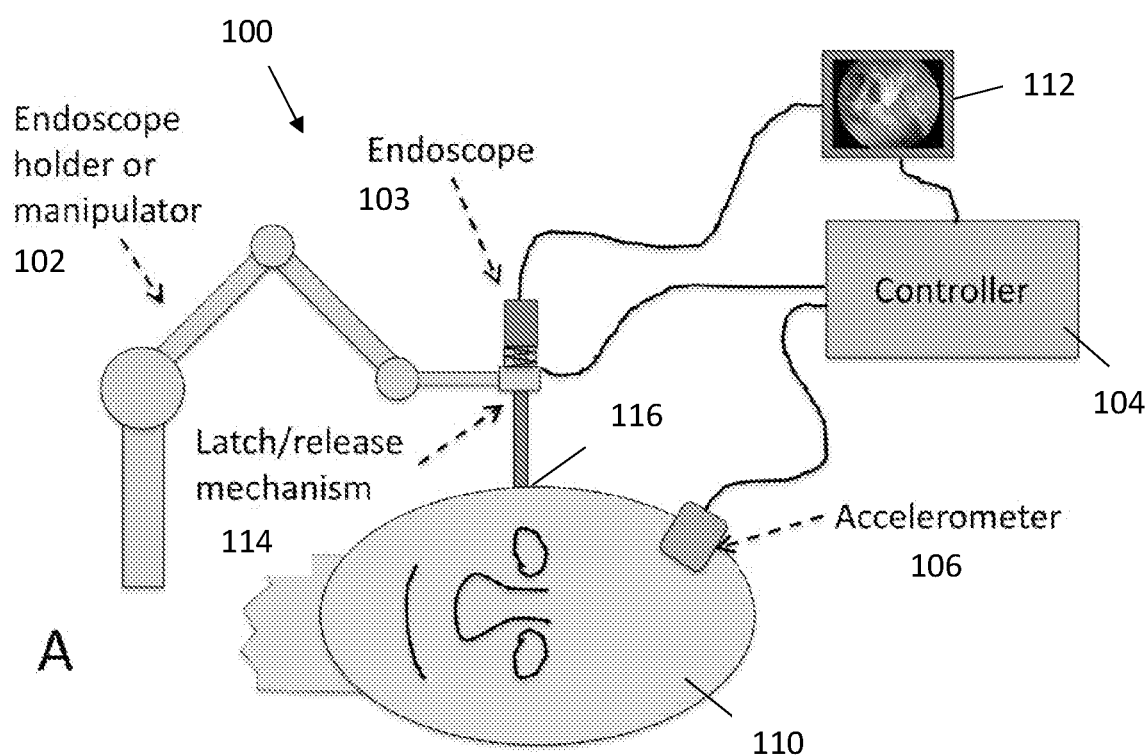
FIG. 1A illustrates a schematic diagram of a head motion detection and automated endoscope/tool retraction in an engaged position.
Figure 1B:
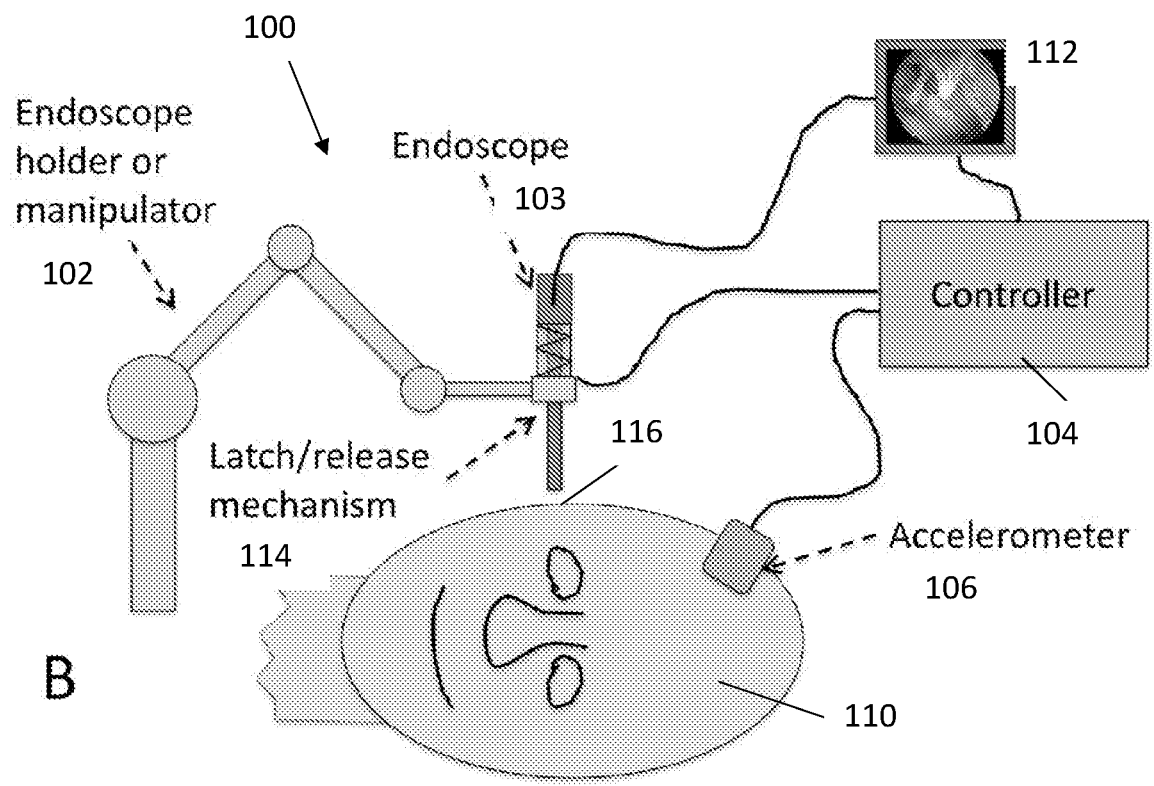
FIG. 1B illustrates a schematic diagram of a head motion detection and automated endoscope/tool retraction in a retracted position, according to an embodiment of the present invention.

FIG. 1A illustrates a schematic diagram of a head motion detection and automated endoscope/tool retraction system in an engaged position. FIG. 1B illustrates a schematic diagram of a head motion detection and automated endoscope/tool retraction in a retracted position, according to an embodiment of the present invention. The system 100 includes an endoscope holder or manipulator 102. An endoscope 103 is disposed within the endoscope holder or manipulator 102. The endoscope holder or manipulator 102 is actuated by controller 104. An accelerometer 106 is positioned on the patient 108. As illustrated in FIGS. 1A and 1B, the accelerometer 106 is positioned on the head 110 of the patient 108 in order to detect movements of the patient's head 110. The accelerometer 106 can be held in position on the head 110 of the patient 108 using a headband, an adhesive, or any other solution known to or conceivable to one of skill in the art. The accelerometer 106 is configured to transmit data related to movement of the patient's head 110 to the controller 104. The system can also include a screen 112 for visualization of the endoscope, its path, and surrounding anatomy. While an accelerometer is described herein any device for tracking patient motion known to or conceivable to one of skill in the art could also be used.

As illustrated in FIGS. 1A and 1B, a latch or release mechanism 114 is included to hold the endoscope in a deployed position. The latch or release mechanism 114 includes a mechanism such as a spring-loaded latch mechanism to hold the endoscope 103 in the deployed position. As illustrated in FIG. 1A the endoscope 103 is held by the endoscope holder or manipulator 102 in the deployed position, such that it is inserted into a small opening 116 (such as the external auditory canal) in the patient's head 110. Any other suitable mechanism for holding the endoscope in the deployed position known to or conceivable to one of skill in the art can also be used. If the accelerometer detects a sudden head motion, the controller releases the latch or release mechanism 114, causing the endoscope 103 to retract back along its longitudinal axis out of the opening 116 in the patient's head 110, as shown in FIG. 1B. It will be readily apparent to one of ordinary skill in the art that alternative embodiments are possible to implement this invention. The key elements are a sensing means to sense patient motion relative to the endoscope body and an apparatus to perform rapid retraction of the endoscope when motion posing a risk of collision between the endoscope and delicate anatomy is detected. These key elements and any supporting elements can take any form known to or conceivable by one of skill in the art.

Figure 2:
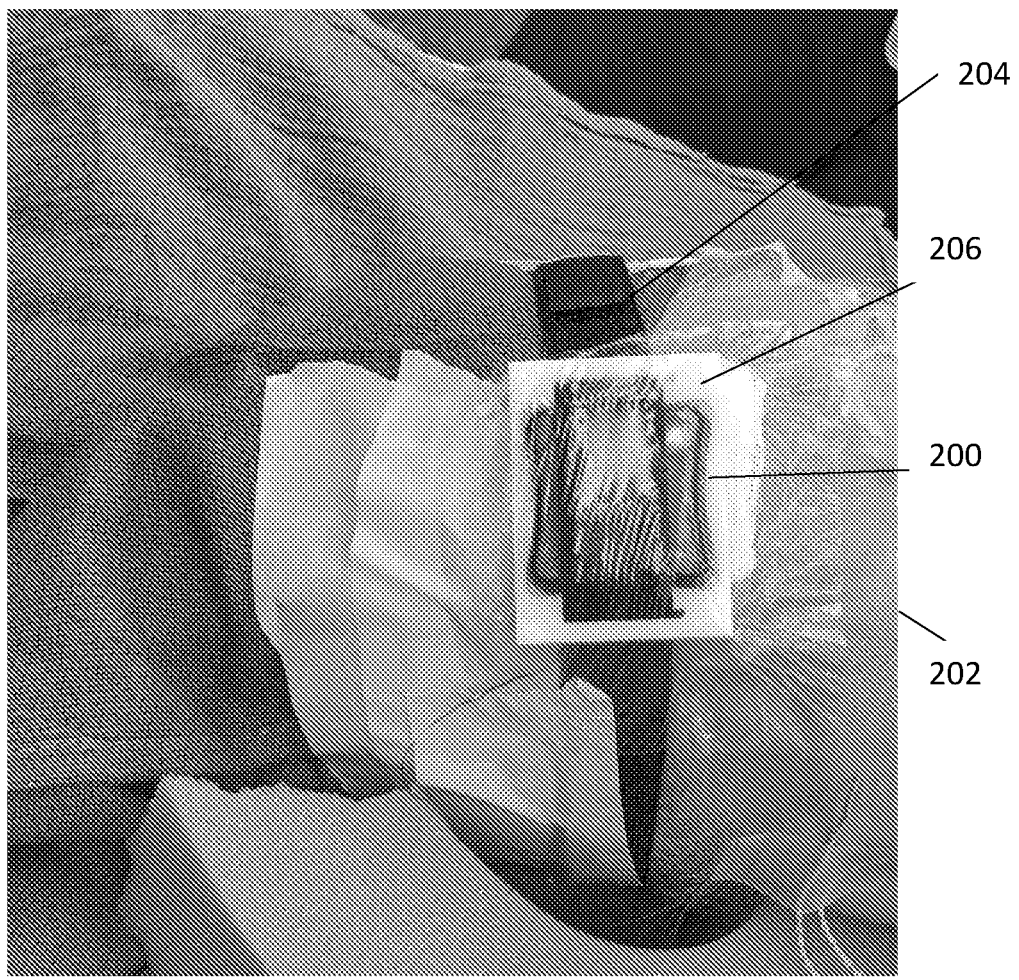
FIG. 2 illustrates a perspective view of an accelerometer and headband, according to an embodiment of the present invention.

FIG. 2 illustrates a perspective view of an accelerometer and headband, according to an embodiment of the present invention. As illustrated in FIG. 2, one preferred embodiment uses an accelerometer 200 to detect patient head motion. One suitable accelerometer is the LPMS-B2 9 axis internal measurement unit (Zenshin Tech, Hong Kong. https://www.zenshin-tech.com), but any accelerometer with sufficient sensitivity and sensing axes to detect patient motion in all possible directions that could result in patient harm can be used. The LPMS-B2 communicates with external controllers via a Bluetooth® wireless connection. This simplifies sterility considerations and also eliminates the need for a cable. However, any suitable means known in the art for communicating with the controller may be used. Examples include: other wireless connections; optical communications; or conventional wire cables. In the preferred embodiment, the accelerometer 200 is secured to the patient's head 202 by means of a tight elastic band 204 with a custom holder 206, as shown in FIG. 2. Depending on the specific tolerances required by the specific application, some small amount of motion between the accelerometer 200 and the patient's head 202 may be acceptable, so long as the motion is small and sudden, safety-significant motions are detected. Alternative means for securing the accelerometer to the head include a mouth guard, adhesives, small screws into the skull, or any other suitable securement known to or conceivable by one of skill in the art.

Other means for detecting patient motion relative to the endoscope may also be used. For example, real time analysis of video images seen through the endoscope provide may be used. Similarly, video analysis using external cameras or optical or electromagnetic surgical navigation systems (such as the Polaris® or Aurora® systems from Northern Digital—Waterloo, Canada, www.ndigital.com) may be used. Alternatively, a sensorized mechanical wand touching the patient's head or motion sensors embedded in the head rest may be used. In yet other embodiments, EMG electrodes may be used to monitor motions of the sternocleidomastoid muscle or other neck musculature to detect patient head motion caused by these muscles.

It is important to note that it is necessary to detect motions of the head relative to the endoscope. If the base of the endoscope holder is fixed relative to the operating table and the holder is reasonably stiff, then it usually suffices to detect head motion alone. Otherwise, relative motion may be detected by placing additional sensors on the endoscope or holder and measuring relative motion between these sensors. Also, some methods (such as video analysis) may detect relative motion directly.

As described above, a simple spring-loaded and latched mechanism may be used to provide very rapid retraction of the endoscope from the patient's head. In this case, it is important that the holding mechanism be designed to hold the endoscope firmly when it is in the "deployed" position and that it constrains motion so that the retraction is along the longitudinal direction of the endoscope path, so as not to damage the patient during retraction. However, other means of retraction may be used to substitute for this mechanism or may be used in combination with it. For example, a fast actuator (e.g., a piston or fast linear motor) may be used to replace the spring actuator. Similarly, in the case where a robotic device is used to hold the endoscope, a programmed motion of the robot to move the endoscope straight out or along another defined, safe path may be used. One example of a robot for head-and-neck surgery that is capable of agile retraction of an endoscope or surgical tool along a straight or pre-defined path is the REMS system.

Further, these motion means may be combined. For example, if the patient motion is sufficient to require retraction, then the robot may be used to perform the retraction, so long as it is fast enough to prevent collision between the endoscope and critical anatomic structures. However, if the patient motion is too fast for the robot, then a spring or other fast retraction mechanism may be used to speed up the withdrawal. Also, it may not always be essential for the retraction motion to completely remove the endoscope or tool from the patient. It may only be necessary to move the tool far enough from critical anatomy so that a damaging collision is avoided.

Although embodiments for safe withdrawal of surgical endoscopes in the case of sudden patient head motion are described herein, it will be readily apparent to one of ordinary skill that this invention may be adapted to provide safe retraction of other tools that may be inserted into the patient's body. Generally, any tool with a long linear shaft may be appropriate for use with this system. Examples include: surgical drills, surgical forceps, suction tools, and irrigators. In these cases, the important thing is that the retraction path be appropriate so that the tool does not damage critical structures during retraction.

It will also be apparent to one of ordinary skill in the art that the invention may also be adapted to other anatomy or clinical applications. For example, the system may be used in endoscopic thyroid surgery, vocal cord surgery, ophthalmology, or spine surgery. Similarly, it may also be adapted to cases where critical factors other than patient motion may require safe, quick retraction of the tool. For example, if a surgical robot is manipulating a surgical drill during otologic procedures, a sensor is often placed to monitor activity of the facial nerve. If the nerve monitor indicates nerve activity caused by the drill, then the system can quickly retract the drill a short distance in order to avoid damaging the nerve. One may also use means known in the art other than an accelerometer to detect sudden patient motion. Examples would include ordinary video tracking through the endoscope or using an auxiliary camera or optical or electromagnetic tracking devices such as commonly used in surgical navigation systems. The device can be coupled to a surgical robot or a passive instrument holder. The device for tracking patient motion includes a means for coupling the device to the patient. Alternately, a computer vision or vision-based tracking system can also be used.

The control function of the present invention can be carried out using a computing device such as a microcontroller, computer, non-transitory computer readable medium, or alternately a computing device or non-transitory computer readable medium incorporated into the robotic device.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention. The operating console for the device is a non-generic computer specifically designed by the manufacturer. It is not a standard business or personal computer that can be purchased at a local store. Additionally, the console computer can carry out communications with the surgical robot through the execution of proprietary custom built software that is designed and written by the manufacturer for the computer hardware to specifically operate the hardware.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention. While exemplary embodiments are provided herein, these examples are not meant to be considered limiting. The examples are provided merely as a way to illustrate the present invention. Any suitable implementation of the present invention known to or conceivable by one of skill in the art could also be used.

What is claimed is:

1. A system for providing safety during surgery comprising:
   an accelerometer configured to track patient motion;
   a surgical device holder, wherein the surgical device holder comprises a latch configured to move a surgical device disposed within the surgical device holder between a deployed position and a retracted position, and wherein the latch is biased to the deployed position; and
   a controller configured to receive information from the accelerometer, wherein the controller is further configured to actuate the latch of the surgical device holder between the deployed position and the retracted position, when the accelerometer detects patient motion.

2. The system of claim 1 wherein the latch of the surgical device holder comprises a spring configured to providing actuation force for a retraction motion.

3. The system of claim 1 wherein the surgical device holder takes the form of an endoscope holder.

4. The system of claim 1 wherein the latch of the surgical device holder is configured to actuate movement of the surgical device along a longitudinal axis of the surgical device.

5. The system of claim 1 further comprising the surgical device holder being configured to be coupled to a surgical robot.

6. The system of claim 1 wherein the surgical device holder takes the form of a surgical robot.

7. The system of claim 1 further comprising a means for coupling the accelerometer to the patient.

8. The system of claim 7 wherein the means for coupling the accelerometer to the patient comprises one selected from a group consisting of an elastic band, an adhesive, and screws.

9. The system of claim 1 wherein the accelerometer comprises wireless communication with the controller.

10. The system of claim 1 wherein the controller comprises wireless communication with the mechanism of the surgical device holder.

11. A system for providing safety during surgery comprising:
- a device for tracking patient motion;
- a surgical device holder, wherein the surgical device holder comprises a latch configured to move a surgical device disposed within the surgical device holder between a deployed position and a retracted position, and wherein the latch is biased to the deployed position; and
- a controller configured to receive information from the device for tracking patient motion, wherein the controller is further configured to actuate the latch of the surgical device holder between the deployed position and the retracted position, when the device for tracking patient motion detects patient motion relative to the surgical device.

12. The system of claim 11 wherein the latch of the surgical device holder comprises a spring configured to provide actuation force for a retraction motion.

13. The system of claim 11 wherein the surgical device holder takes the form of an endoscope holder.

14. The system of claim 11 wherein the latch of the surgical device holder is configured to actuate movement of the surgical device along a longitudinal axis of the surgical device.

15. The system of claim 11 further comprising the surgical device holder being configured to be coupled to a surgical robot.

16. The system of claim 11 wherein the surgical device holder takes the form of a surgical robot.

17. The system of claim 11 wherein the device for tracking patient motion includes a means for coupling the device to the patient.

18. The system of claim 11 wherein the device for tracking patient motion comprises one selected from a group consisting of an accelerometer, video camera, auxiliary camera, and optical or electromagnetic tracking device.

19. The system of claim 11 wherein the device for tracking patient motion comprises wireless communication with the controller.

20. The system of claim 11 wherein the controller comprises wireless communication with the mechanism of the surgical device holder.

* * * * *